United States Patent [19]

Galwey et al.

[11] Patent Number: 4,500,840
[45] Date of Patent: Feb. 19, 1985

[54] HIGH SPEED, POWER POTENTIOSTAT/GALVANOSTAT WITH IR COMPENSATION FOR USE WITH AN ELECTROCHEMICAL CELL

[75] Inventors: Ronald K. Galwey, Los Gatos; Kay K. Kanazawa, San Jose, both of Calif.

[73] Assignee: International Business Machines Corporation, Armonk, N.Y.

[21] Appl. No.: 437,412

[22] Filed: Oct. 28, 1982

[51] Int. Cl.³ ............................................. G01N 27/42
[52] U.S. Cl. ................................... 324/425; 204/231; 204/406
[58] Field of Search ............... 324/425, 439, 446, 450; 204/231, 406

[56] References Cited

U.S. PATENT DOCUMENTS 3,398,064  8/1968  Propst ................................. 324/425
4,305,039  12/1981  Steuernagel et al. ............... 324/425
4,348,632  9/1982  Galwey et al. ...................... 204/231

Primary Examiner—Michael J. Tokar
Assistant Examiner—Kevin D. O'Shea
Attorney, Agent, or Firm—Joseph E. Kieninger

[57] ABSTRACT

An electrochemical instrument for use with an electrochemical cell that provides IR compensation while operating as either a galvanostat or a potentiostat. The instrument includes an electronic circuit having two output terminals, an input differential amplifier circuit, an output differential amplifier circuit, a control differential amplifier circuit, a reference differential amplifier circuit, a resistor, electric circuitry connecting the input terminal of the control amplifier to the instrument output terminal and a double pole, double throw switch means. In a preferred embodiment, the electric circuitry connecting the control amplifier to the instrument output terminal is a potentiometer.

6 Claims, 4 Drawing Figures

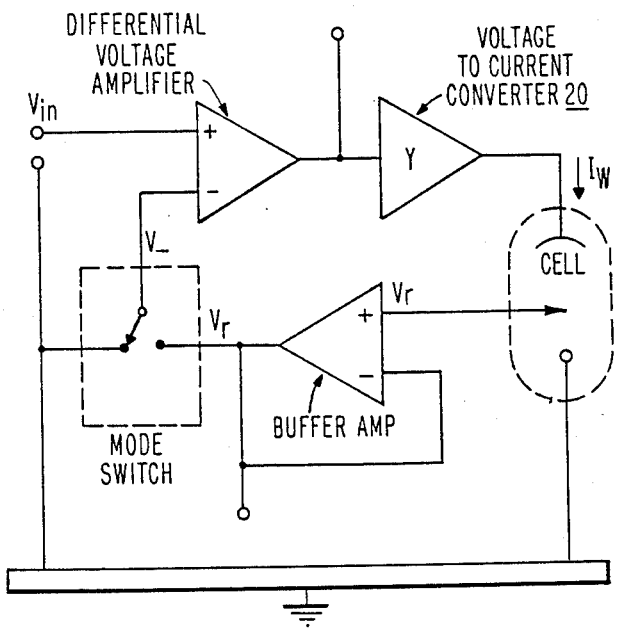
PRIOR ART
FIG. 1
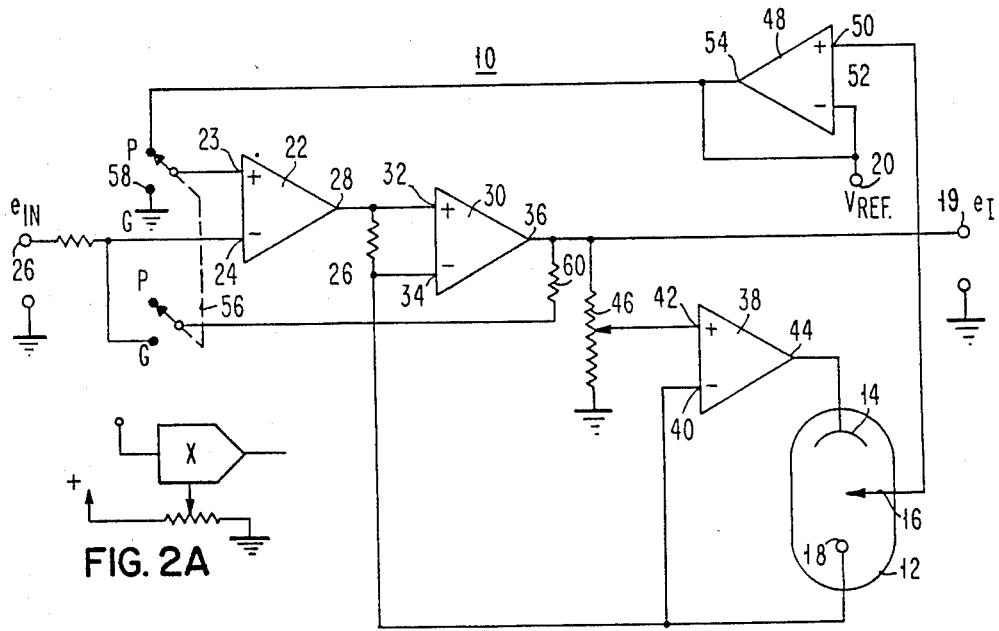
FIG. 2A
FIG. 2B
FIG. 2

HIGH SPEED, POWER POTENTIOSTAT/GALVANOSTAT WITH IR COMPENSATION FOR USE WITH AN ELECTROCHEMICAL CELL

TECHNICAL FIELD

This invention relates to a potentiostat/galvanostat for use with an electrochemical cell and more particularly to a potentiostat/galvanostat with IR compensation.

BACKGROUND ART

Electrochemical cells are widely used for electrochemical and biological applications. Typically, an electrochemical cell has a counter electrode at the top of the cell, a non-current-carrying reference electrode positioned in the central region of the cell and a working electrode positioned near the bottom of the cell. Controlling and measuring the electrical parameters of an electrode reaction in a cell is done by potential, current and charge control means. The two most common modes of operation are potential control or potentiostatic mode and the current control or galvanostatic mode. A review article by R. Greef, covering this subject matter is published in *Journal of Physics E, Scientific Instruments*, Vol. 11, 1978, pages 1–12 (printed in Great Britain).

When operating a potentiostat or a galvanostat with an electrochemical cell, there is a voltage drop, that is, an IR drop across the reference electrode and the working electrode. For example, whereas the voltage at the reference electrode may be 1.00 v, the corresponding voltage at the surface of the working electrode is 0.80 v. In this case, the IR drop is 0.20 volts. In order to make accurate measurements, it is necessary to provide IR compensation when operating the potentiostat and the galvanostat.

Electrochemical instruments that are available commercially that perform both as potentiostats and galvanostats can perform the IR compensation when operating as a potentiostat, but they do not perform the IR compensation when operated at a galvanostat. Thus, there is no IR compensation available for operation in the galvanostatic mode.

With high power potentiostat/galvanostat usage, high current is employed. The voltage drop across the reference electrode and working electrode across the uncompensated resistance can be extremely large.

Commercially available potentiostat/galvanostats of the type described in the instruction manual for the Princeton Applied Research Model 173 Potentiostat/Galvanostat have a number of switches in order to change the instrument from a potentiostatic operating mode to a galvanostatic operating mode. In a power potentiostat/galvanostat, the current flow through some of these switch contacts are large. Another approach to a potentiostat/galvanostat requiring less switches and which requires negligibly small currents flowing through the switch contacts, is shown in FIG. 1 and described in the copending patent application assigned to the assignee of the present invention entitled "An Improved Instrument for Use with an Electrochemical Cell" Ser. No. 049,525 filed June 18, 1979. However, neither of these prior art potentiostat/galvanostat systems provides IR compensation in the galvanostatic mode; and FIGS. 2A and 2B are alternative embodiments of electric circuitry 46 of FIG. 2.

SUMMARY OF THE INVENTION

An electrochemical instrument for use with an electrochemical cell that provides IR compensation while operating as either a galvanostat or a potentiostat. The instrument includes an electronic circuit having two output terminals, an input differential amplifier circuit, an output differential amplifier circuit, a control differential amplifier circuit, a reference differential amplifier circuit, a resistor, electric circuitry connecting the input terminal of the control amplifier to the instrument output terminal and a double pole, double throw switch means. In a preferred embodiment, the electric circuitry connecting the control amplifier to the instrument output terminal is a potentiometer.

For a further understanding of the invention and of the objects and advantages thereof, reference will be had to the following detailed description and to the accompanying drawings and to the appended claims wherein the specific embodiments of the invention are shown.

BRIEF DESCRIPTION OF THE DRAWINGS

The invention will now be described by way of example and reference to the accompanying drawings in which:

FIG. 1 is a schematic view illustrating the prior art instrument suitable for operation in both the potentiostatic and galvanostatic mode; and FIG. 2 is a schematic view illustrating a preferred embodiment of an improved instrument and circuitry in accordance with this invention.

DESCRIPTION OF THE PREFERRED EMBODIMENT

As shown in FIG. 2, the electronic circuit 10 of a potentio/galvanostat is used for analyzing the operation of an electrochemical cell 12. The electrochemical cell 12 has a counter electrode 14, a reference electrode 16 and a working electrode 18. The circuit contains potentiostat/galvanostat instrument output first and second terminals 19 and 20. The input differential amplifier circuit 22 has a first input terminal 24 to which a test potential waveform is applied. A resistor 26 is connected between the output terminal 28 of the input amplifier circuit 22 and the working electrode 18 of the cell 12. An output differential amplifier circuit 30 has input terminals 32 and 34 individually connected across the resistor 26. Circuit 30 has an output terminal 36 connected to one of the instrument output terminals 18.

A control differential amplifier circuit 38 has one input terminal 40 connected to the working electrode 18 of the cell 12. The control circuit 38 has another input terminal and it has an output terminal 44 connected to the counter electrode 14 of the cell 12. There is electric circuitry 46, for example a potentiometer, connecting the second input terminals 42 of the control amplifier 38 to the first instrument output terminal 19. The electric circuitry may be a potentiometer as shown in the drawing, or it may be any linear voltage transfer device such as an analog multiplier 47 as shown in FIG. 2A, or a multiplying D/A converter 49 as shown in FIG. 2B.

A reference differential amplifier circuit has an input terminal 50 connected to the reference electrode 16 of the cell 12. The reference amplifier circuit 48 has another input terminal 52 connected to the other instrument output terminal 20. The reference differential amplifier circuit has an output terminal 54 connected to the second input terminal 52 of the reference differential amplifier circuit.

A double pole, double-throw electric or electronic switch 56 selectively connects the second input terminal 23 of the input amplifier circuit 22 to the output terminal 54 of the reference differential amplifier circuit 48 and to ground. When the switch 56 is connected to ground, the first input terminal 24 is connected through a resistor 60 to the first instrument output terminal 19.

The novel features in this electronic circuit include the use of a variable portion of the potential $e_I$ which is proportional to the cell current that is applied to the noninverting input 42 of control differential amplifier circuit 38 to provide IR compensation in both potentiostatic and galvanostatic modes. The degree of IR compensation is determined in the potentiostatic mode and the same degree of compensation is maintained in the galvanostatic mode.

The resulting simplicity in switching from one mode to the other is apparent from FIG. 2. The current through the switch 56 in either mode is negligible and the "on resistance" value is unimportant, permitting the use of solid state mode i.e. electronic switching. Additional features present in this design are that the input and output connectors maintain their same function in both modes. The IR compensation response has been shown to be smooth, easy to adjust in the potentiostatic mode, and to be maintained in the galvanostatic mode.

The potential which is experimentally accessible (the potential difference between the reference electrode and the working electrode) includes the IR drop across the solution resistance R between the reference and working electrodes due to the cell current I. Of greatest practical interest is the behavior between the cell current and the potential difference mentioned above, except NOT including the IR drop. The distortion caused by this IR drop can be appreciable and can preclude any meaningful interpretation of data in either potentiostatic or galvanostatic operation. For example, during electrolytic plating under galvanostatic conditions, the true driving potential would be masked by the unknown IR drop.

Although a preferred embodiment of this invention has been described, it is understood that numerous variations may be made in accordance with the principal of this invention.

What is claimed is:

1. An electronic circuit for analyzing the operation of electrochemical cells of the type having a counter electrode, a reference electrode, and a working electrode in terms of potential and current modes of operation selectively, said circuit comprising first and second instrument output terminals;

an input differential amplifier circuit having a first input terminal to which a test potential waveform is applied having a second input terminal, and having an output terminal;

a resistor connected between the output terminal of the input amplifier circuit and the working electrode of the cell;

an output differential amplifier circuit having input terminals individually connected across the resistor and having an output terminal connected to a first instrument output terminal;

a control differential amplifier circuit having a first input terminal connected to the working electrode of the cell, having a second input terminal and having an output terminal connected to the counter electrode of the cell;

electric circuitry connecting the second input terminal of the control amplifier to the first instrument output terminal; a reference differential amplifier circuit having a first input terminal to the reference electrode of the cell, having a second input terminal connected to the second instrument output terminal and having an output terminal connected to the second input terminal of the input differential amplifier circuit; and a double-pole, double-throw switch means for selectively connecting the second input terminal of the input amplifier circuit to the output terminal of the reference amplifier circuit or to ground and in the latter case for connecting the first input terminal through a resistor to the first instrument output terminal.

2. A circuit as described in claim 1 wherein said electric circuitry is a potentiometer.

3. A circuit as described in claim 1 wherein said electric circuitry is an analog multiplier.

4. A circuit as described in claim 1 wherein said electric circuitry is a multiplying D/A converter.

5. A circuit as described in claim 1 wherein said switch means is electrical.

6. A circuit as described in claim 1 wherein said switch means is electronic.

* * * * *